United States Patent [19]
Watkins

[11] 4,000,949
[45] Jan. 4, 1977

[54] PHOTOMASK INSPECTION BY OPTICAL SPATIAL FILTERING

[75] Inventor: Laurence S. Watkins, Hopewell, N.J.

[73] Assignee: Western Electric Company, Incorporated, New York, N.Y.

[22] Filed: Sept. 15, 1969

[21] Appl. No.: 858,002

[52] U.S. Cl. .................. 356/165; 350/162 SF; 356/71
[51] Int. Cl.² .............. G01B 9/08; G02B 27/00
[58] Field of Search .......... 356/156, 165, 71, 166, 356/168; 350/162

[56] References Cited
UNITED STATES PATENTS

| | | | |
|---|---|---|---|
| 3,064,519 | 11/1962 | Shelton | 356/71 |
| 3,240,108 | 3/1966 | Lehan et al. | 350/162 X |
| 3,435,244 | 3/1969 | Burckhardt et al. | 250/219 |
| 3,614,232 | 10/1971 | Mathisen | 356/109 |

OTHER PUBLICATIONS

O'Neill, E. L., "Spatial Filtering in Optics," IRE Transactions on Information Theory, June 1956, pp. 56–64.

Primary Examiner—Ronald J. Stern
Attorney, Agent, or Firm—J. Rosenstock

[57] ABSTRACT

An intensity-type optical spatial filtering system is arranged to form a composite visual image of all nonperiodic errors in a photomask or other two-dimensional pattern which contains an array of regularly spaced, normally identical elements. A coherent beam of light is diffracted by the pattern and focused onto a transparency having a second array of discrete opaque regions spaced by a distance inversely proportional to the element spacing on the pattern. The focused light, spatially modulated by the transparency, is reimaged and projected in enlarged form onto a display screen.

7 Claims, 10 Drawing Figures

INVENTOR
L. S. WATKINS

BY

ATTORNEY

PHOTOMASK INSPECTION BY OPTICAL SPATIAL FILTERING

BACKGROUND OF THE INVENTION

As is well known, photomasks employed in the large-scale manufacture of semiconductor devices and integrated circuits may take the form of transparencies which contain regular arrays of normally identical optical elements each representative of an individual device or circuit. Typically, each element on a mask is a photographic image produced by optical reduction from a master image in a conventional "step and repeat" operation.

Evidently, any defects in the images on the mask will lead to corresponding defects in the associated devices or circuits fabricated with the use of the mask. Generally, such mask defects are of a nonperiodic nature, wherein defects appearing in a single element of the array have no discernible relation to any other element of the array. To avoid the manufacture of defective devices and circuits of this nature, it is important that all the images on the associated mask be examined for such errors before the mask is employed in production. Unfortunately, visual inspection of the mask, even with the aid of a microscope, projector, or similar device, is time consuming and tedious; this is particularly true when, as in the usual case, the mask may contain hundreds of closely spaced, minute elements. The same drawback is present, of course, when inspecting other types of two-dimensional patterns containing regular arrays of elements, such as grids for television-augmented telephone sets supplied under the name PICTUREPHONE by Western Electric Company, Inc.

SUMMARY OF THE INVENTION

This drawback is eliminated in large part by the technique of the present invention, which may be used to simultaneously inspect all of the elements on a photomask or other two-dimensional pattern containing a regular array of normally identical elements, and produce a composite optical image of all nonperiodic errors therein. The apparatus employs optical spatial filtering of the intensity type to exploit the ideally repetitive nature of the elements forming the array on the pattern.

It is known that such a periodic array of optical elements acts as a grating which, when subjected to a spatially coherent beam of light, yields a composite diffraction pattern whose spatical distribution is the optical product of two components: (1) the interference function of the array, consisting of a distribution of bright spots whose spacing is inversely proportional to the distance between adjacent elements of the pattern; and (2) the diffraction pattern of a single element.

In an illustrative arrangement of this type suitable for inspecting an array-type photomask, coherent light that is intensity-spactially modulated by the mask is focused on a planar optical filter to form the diffraction pattern of the mask. The filter, which operates on the intensity characteristic of the incident diffraction pattern, comprises a transparency that includes a plurality of discrete opaque regions (illustratively round dots) on a transparent field, the dots being spaced by a distance inversely proportional to the element spacing on the mask. The incident diffraction pattern is spatially modulated by the filter and then refocused to yield an image whose amplitude distribution is simultaneously representative of all the nonperiodic errors on the mask. The projection of such focused image on a display screen exhibits a likeness of each such nonperiodic defect in its true relative position on the mask.

The spatial distribution of the opaque regions in the optical filter may, in one embodiment, follow the spatial pattern of bright spots defined by the array interference pattern. Alternatively, the distribution of opaque regions on the filter may follow the spatial pattern of bright spots defined by the optical product of the interference function of the array and the diffraction pattern of a single mask element.

BRIEF DESCRIPTION OF THE DRAWING

The nature of the invention and its advantages will appear more fully from the following detailed description taken in conjunction with the appended drawing, in which.

DETAILED DESCRIPTION

Figure 1:
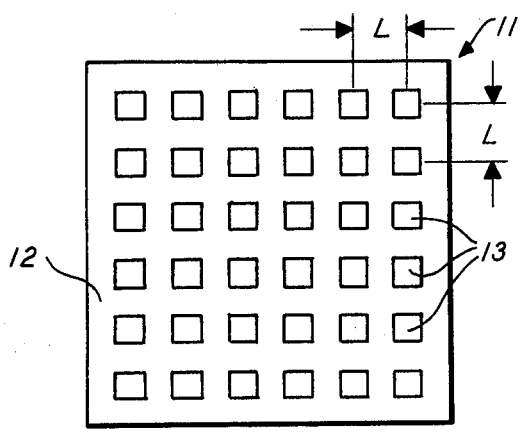
FIG. 1 is a pictorial representation of a photomask transparency having a periodic array of normally identical optical elements.

Referring now to the drawing, FIG. 1 shows a typical integrated circuit mask 11 comprising a transparency 12, such as photographic film, which contains a square planar array of theoretically identical photographic images 13—13 (hereafter "elements 13"). Illustratively, the array consists of six rows of elements, with six elements appearing in each row and spaced by a nominal center distance L. For purposes of this description, the distance L is assumed to be invariant from element to element.

Figure 2:
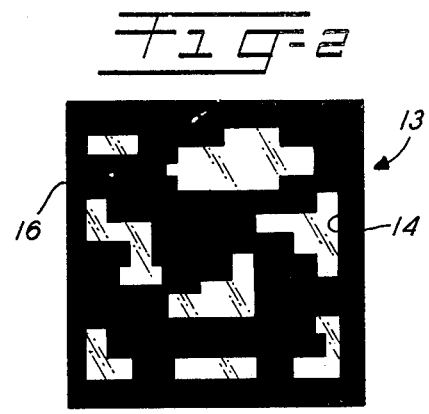
FIG. 2 is an enlarged view of one element on the mask of FIG. 1.

As shown in FIG. 2, each element 13 defines a prescribed circuit configuration corresponding to that of the resulting integrated circuit. Such configuration is characterized by a predetermined optical-density distribution which, in the particular case illustrated, comprises a plurality of optically transparent areas 14—14 against an opaque background 16.

In practice, the array of elements 13 depicted in FIG. 1 is not ideal and is subject to defects which, if undetected, result in errors in the finished circuits. Such errors may take several forms. One form, which will be denoted "periodic errors," exhibits similar characteristics from element to element; such periodic errors might be due, e.g., to defects in the master image (not shown) which is used to produce the elements on the mask by optical reduction in a "step-and-repeat" process. It will be assumed that no such periodic errors appear in the illustative mask 11.

A second and more prevalent class of errors will be denoted "nonperiodic," wherein defects in one element are not identically repeated in the remaining elements. In general, such nonperiodic errors are random or quasi-random in nature, such as missing or extra element features, nonprogressive positional errors, poor localized edge definition, scratches, pinholes caused by dirt, air bubbles formed on the mask during development of the elements, and localized defects in the photographic emulsion employed. However, such nonperiodic errors, for purposes of this description, may also include progressivve positional errors such as those caused by eccentricities in the step-and-repeat apparatus itself whereby, for example, the center distance between successive ones of the elements 13 in the array progressively increases or decreases by an increment proportional to the nominal spacing L.

Figure 3:
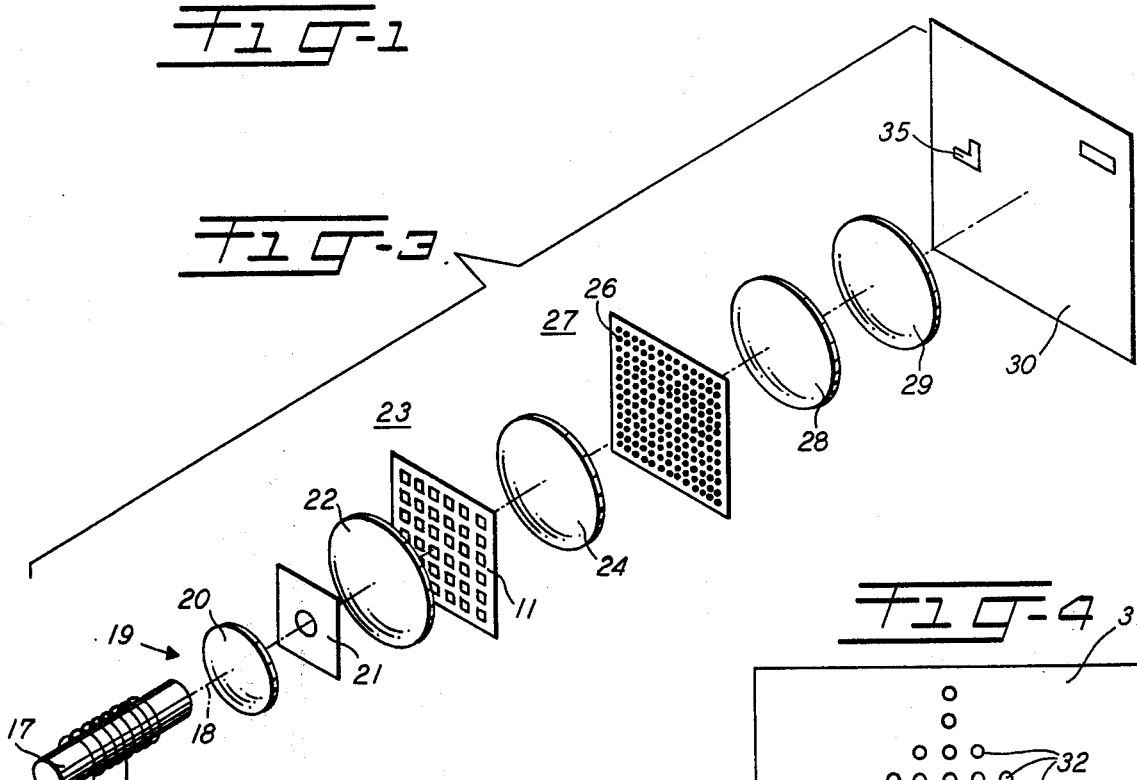
FIG. 3 is an optical system for simultaneously inspecting all of the elements on the mask of FIG. 1 for nonperiodic errors.

One technique for simultaneously detecting all nonperiodic errors within the array of elements 13 of the mask 11 may be carried out with the apparatus shown in FIG. 3. Except as indicated below, the apparatus illustrated defines an optical-spatial filtering system of the general type shown, e.g., in FIG. 1 of U.S. Pat. No. 3,435,244, issued to C. B. Burckhardt et al. on Mar. 25, 1969. Coherent monochromatic light from a laser 17 is directed along a longitudinal axis 18 and through a beam expander 19 comprising a first lens 20 and a pinhole mask 21. The light emanating from the mask 21 passes through a second lens 22 which collimates the light into a plane parallel beam. Such beam is directed through a planar optical workpiece 23 (which in this case is the mask 11 of FIG. 1,) and the optical grating effect of the element array on the mask 11 diffracts the beam into an intensity-modulated pattern characteristic of the array. A third convex lens 24 focuses the diffraction pattern of the mask on a planar optical filter 26 (described below) disposed at a focal plane 27 of the lens 24. The filter 26 is of the intensity type, e.g., a type responsive only to the spatial amplitude distribution of the light incident thereon from the lens 24.

The filter 26 spatially modulates the light incident thereon; and since such incident light is itself a focused diffraction pattern characteristic of the array of elements 13 on the mask 11, the light transmitted through the filter 26 is a cross-correlation of the array and the filter patterns. Such transmitted light, when properly focused by a fourth reimaging convex lens 28, accordingly defines a reconstructed image of the mask 11 less any information blocked by the filter 26. A fifth lens 29 is positioned beyond the lens 28 by a distance slightly greater than the sum of their focal lengths to project the focused reconstructed image in enlarged form onto a display screen 30.

Figure 5:
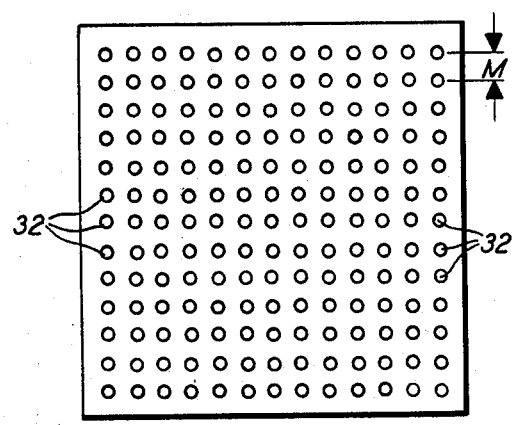
FIG. 5 is a pictorial diagram of the interference function of the mask of FIG. 1.
Figure 4:
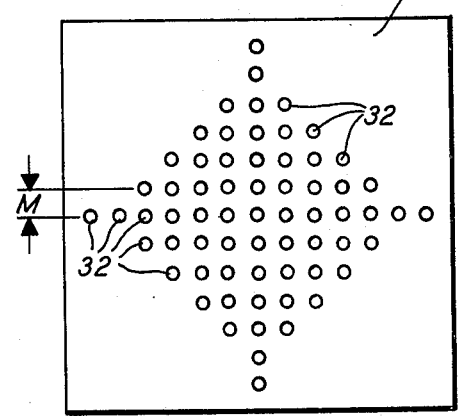
FIG. 4 is a pictorial diagram of the composite diffraction pattern of the mask of FIG. 1.

A properly focused diffraction pattern formed by a spatially coherent beam of light when passing through the array mask 11 having no errors therein is shown in FIG. 4. Such pattern, represented at 31, is the optical product of (a) the interference pattern of the array, consisting of a regular distribution of light spots 32—32 mutually spaced by a center distance M inversely proportional to the element spacing L, and (b) the diffraction pattern of a single one of the elements 13 (FIG. 1). It will be appreciated that if each of the elements 13 were optically homogeneous and of negligible size, the resulting diffraction pattern would be the interference function itself; such function is shown in FIG. 5. Thus, the effect of having a prescribed finite circuit configuration for each element 13 as shown, e.g., in FIG. 2, is to intensity-modulate the regular array of light spots 32 making up the interference function of FIG. 5 into the modulated distribution shown in FIG. 4. It will be noted, however, that the center distance between adjacent light spots in FIGS. 4 and 5 is the same.

Figure 6:
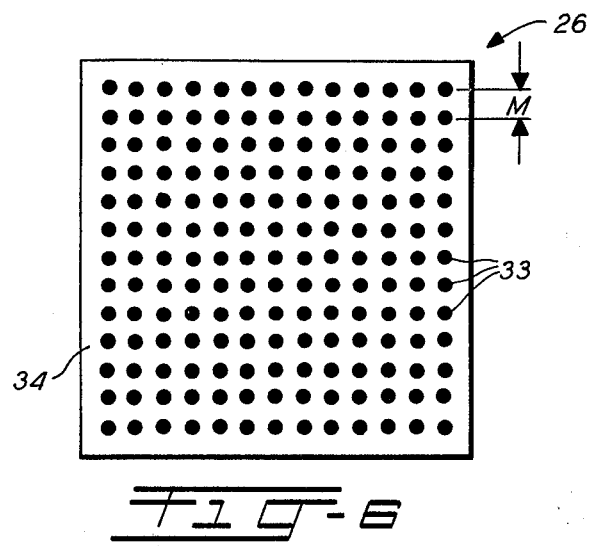
FIG. 6 is a pictorial diagram of an interference function-filter suitable for use in the arrangement of FIG. 3.

In accordance with the invention, the spatial amplitude distribution of one form of the optical filter 26 in the spatial-filtering system of FIG. 3 has the form shown in FIG. 6, i.e., the complement of the interference function of FIG. 5. In particular, the filter 26 (FIG. 6) is a transparency containing a plurality of discrete opaque regions 33—33 disposed on a transparent background 34 and spaced by the distance M. Such opaque regions, which are illustratively round dots but may take various other shapes, such as squares, teardrops, etc., are spatially distributed in accordance with the distribution of the light spots 32 in the interference function of FIG. 5. Such a filter may be constructed with the aid of theoretical calculations based on the grating effect of the array; alternatively, the filter may be empirically produced by exposing and developing a suitable photographic film at the focal plane 27 (FIG. 3) when the workpiece 23 is a mask (not shown) having an array of transparent dots or pinholes against a dark background, such dots being mutually spaced by the element center distance L.

Such an interference-function filter acts as a periodic comparator which blocks the transmission of light which is spatially distributed in the form of bright spots seperated by the center distance M; such spatial distribution, in turn, is characteristic of both the interference function and the diffraction pattern of a "standard" mask. (For present purposes, a 'standard" mask is a mask which has the configuration shown in FIG. 1 and which is found to be relatively free from nonperiodic errors upon conventional visual inspection.)

With this arrangement, when a "standard" mask is employed as the workpiece 23 in the system of FIG. 3, the spatial distribution of light spots of the focused diffraction pattern incident on the focal plane 27 will be exactly coincident with the spatial distribution of opaque dots on the interference-function filter 26. In such a case, a perfect blockage of light will occur and no light will be transmitted to the display screen 30 through the lenses 28 and 29. On the other hand, if the mask 11 inserted in the system of FIG. 3 at the plane of the workpiece 23 exhibits nonperiodic errors, the spatial distribution of the light incident on the filter 26 will not coincide with the distribution of opaque dots across the filter. The residual light spatially modulated by the filter 26 will, after passing through the reimaging lenses 28 and 29, define discrete brightened images (illustratively represented at 35—35) of all the nonperiodic errors in the workpiece 23. Such images, moreover, will appear in the same relative positions on the screen as they appear on the workpiece.

An additional advantage when employing the interference-function filter of FIG. 6 is its capability of isolating nonperiodic errors in the mask 11 irrespective of the exact configuration of the individual elements 13, provided only that the center distance between such elements is maintained at the spacing L. Hence, the same filter can be used to inspect a wide variety of device and circuit patterns in a two-dimensional array.

Figure 7:
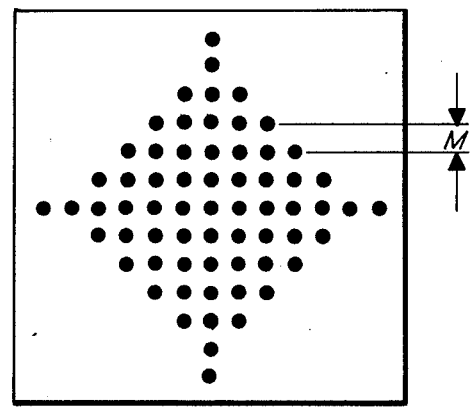
FIG. 7 is a pictorial diagram of a diffraction-pattern filter suitable for use in the arrangement of FIG. 3.

An alternative form of the filter 26 is shown in FIG. 7. This form of filter has an amplitude distribution of opaque dots which defines the complement of the mask-diffraction pattern shown in FIG. 4. Such a diffraction-pattern filter may be conveniently constructed by exposing a suitable photographic plate at the focal plane 27 when a "standard" mask 11, as defined above, is employed as the workpiece 23. In such a case, the laser 17 is energized to expose the photographic plate, after which the plate is removed and developed to form the pattern shown in FIG. 7.

It is apparent that this second form of filter 26 may also be constructed on the basis of theoretical calculations of the diffraction pattern of a perfect mask 11, particularly where the elements 13 have a mathematically simple optical-density distribution.

Since the diffraction pattern of FIG. 4 contains information not only pertinent to the array or grating effect of the mask, but also to the detail of the particular configuration used for the elements 13, this second type of filter is inherently more restricted in application then the interference-function filter of FIG. 6.

It will be appreciated that relatively fine types of nonperiodic errors in the mask 11, such as defects in edge definition, may be accentuated on the screen 30 by placing an auxiliary high-pass optical filter (not shown) adjacent the focal plane 27 in alignment with the filter 26. Such an auxiliary filter may take the form of an opaque disc centered on the optical axis of the system of FIG. 3. The diameter of such disc is suitably chosen, in a manner well known in the art, to block only the relatively low spatial frequencies in the mask-diffraction pattern (manifested by bright spots at and near the optical axis).

In like manner, relatively gross errors may be accentuated by analagously employing as auxiliary low-pass spatial filter, which may take the form of an opaque disc having a central aperture for freely transmitting the relatively low spatial frequencies near the optical axis while blocking the high spatial frequencies farther removed from the axis.

The mask forming the workpiece does not have to be rectilinearly aligned with the axis 18, and, in fact, the mask may be rectilinearly displaced for scanning purposes. While the angular orientation of the workpiece with respect to the mask is more critical, the display on the screen 30 may be made sensibly independent of such angular orientation by employing the compensation technique described in connection with FIGS. 3-12 of the above-mentioned Burckhardt et al. patent. In this latter case, however, the rectilinear mask alignment becomes more critical.

Figure 8:
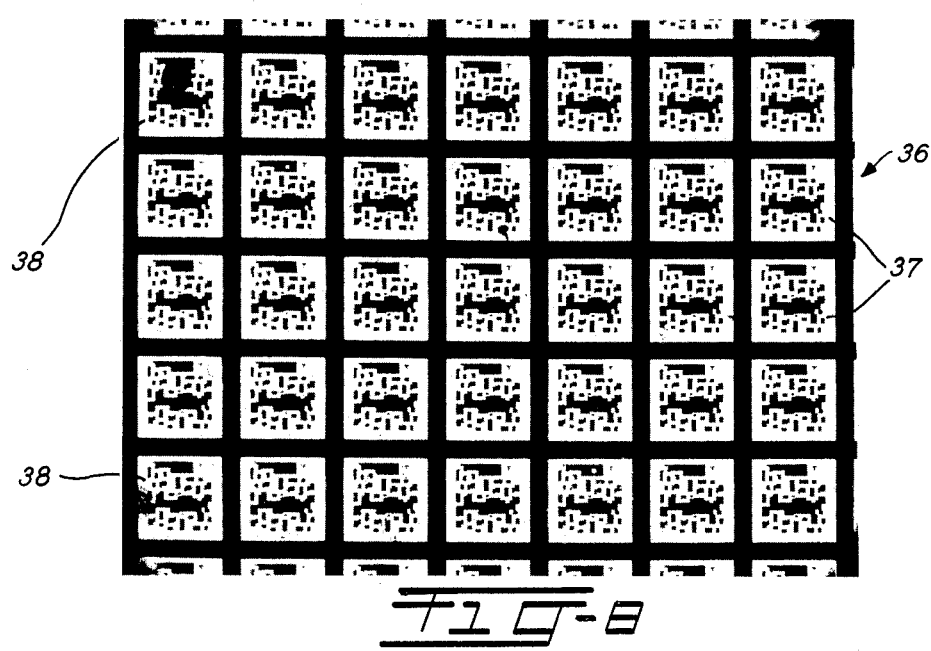
FIG. 8 is a photograph of a first actual array-type photomask having nonperiodic errors therein.
Figure 9:
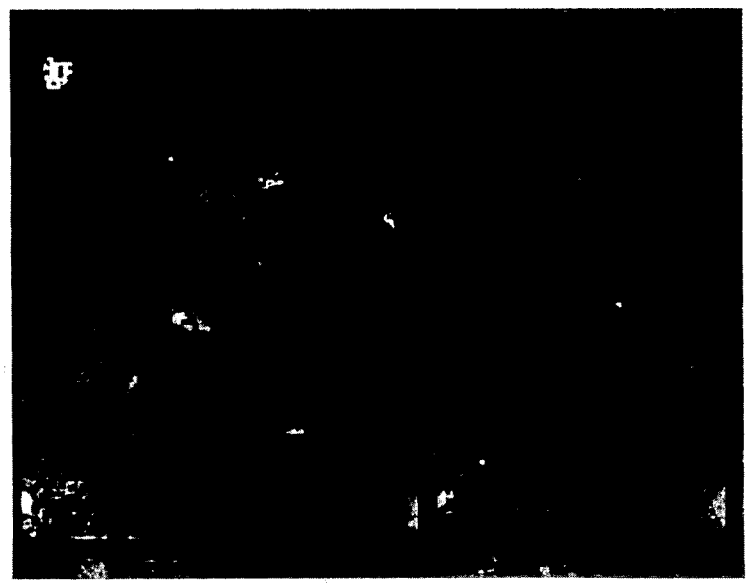
FIG. 9 is a photograph of an image of the nonperiodic errors on the mask of FIG. 8, which image is generated with the aid of the interference-function filter.

FIGS. 8 and 9 illustrate typical results obtained when using the technique of the invention in connection with an interference-function filter of the type shown in FIG. 6 to simultaneously detect nonperiodic errors in a photomask array. FIG. 8 shows a damaged test photomask 36 having an array of normally identical elements 37. Several of the more significant random defects on the mask are illustrated at 38—38. The element center spacing on the mask was nominally 62 mils.

Theoretical calculations on the array or grating factor of such a mask indicated that the bright spots of the corresponding interference function, when focused by a lens having a 100 mm. focal length and when employing a 6328A light wavelength, would be mutually spaced apart by a center distance of 1.6 mils. From these calculations, a filter having a two-dimensional array of opaque round dots spaced by a corresponding center distance of 1.6 mils was constructed on a transparent film. The dot diameter was selected to be 0.8 mils.

The mask 36 of FIG. 8 was employed as the workpiece 23 in the arrangement of FIG. 3, and the interference-function filter just described was disposed at the focal plane 27 of the lens 24. A beam of light from a 15 milliwattt 6328A laser was modulated by the mask 36 and the corresponding diffraction pattern was focused on the filter. The resulting display, on the screen 30, of the nonperiodic errors in the workpiece is shown in FIG. 9.

Figure 10:
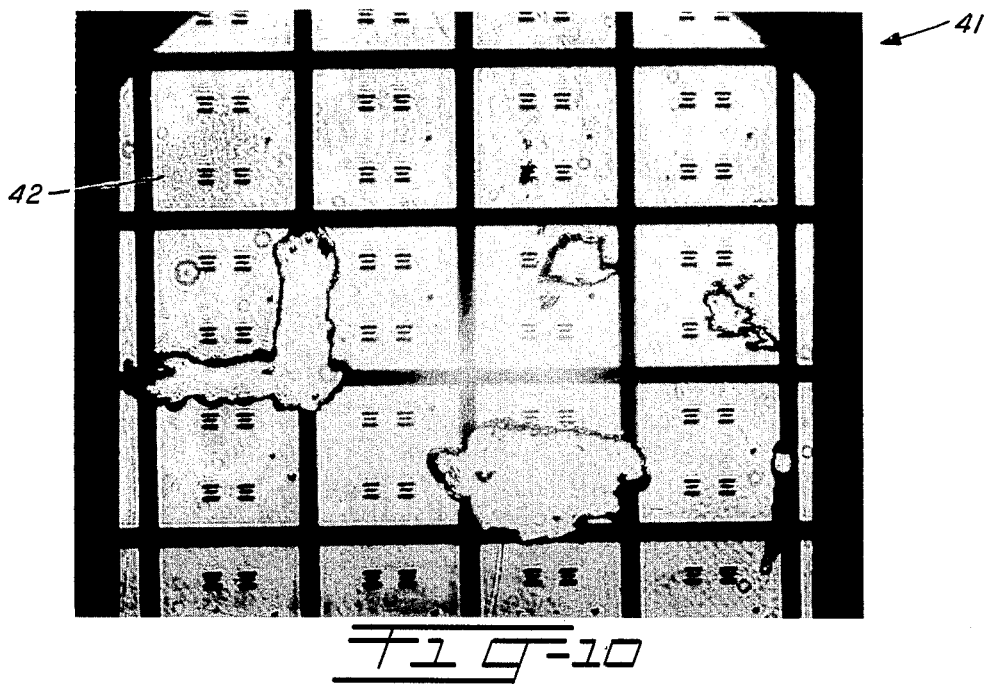
FIG. 10 is a photograph of a second actual array-type photomask having nonperiodic errors therein.
Figure 11:
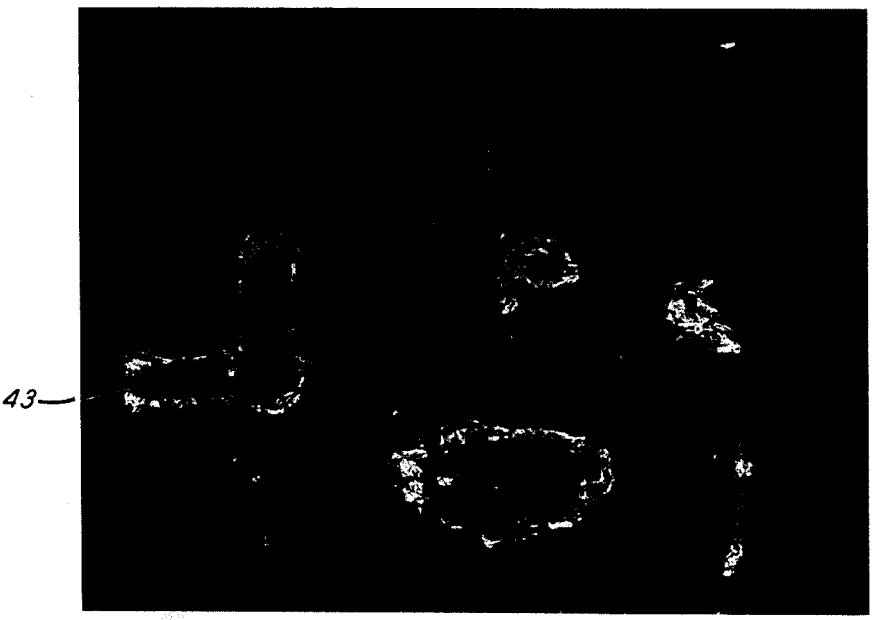
FIG. 11 is a photograph of an image of the non-periodic errors on the mask of FIG. 10, which image is generated with the aid of the diffraction-pattern filter.

FIGS. 10 and 11 illustrate typical results obtained when using the technique of the invention in connection with a diffraction-pattern filter of the type shown in FIG. 7 to detect nonperiodic errors in a photomask array. FIG. 10 shows a damaged mask 41 having an array of normally identical elements 42—42 each defined by four sets of small horizontal lines as shown. The maximum thickness of each small line is about 0.4 mils, while the center distance between elements in the array is about 20 mils.

The required optical filter was constructed using a "standard" mask having a relatively error-free array pattern of the type shown in FIG. 10 as the workpiece in the arrangement of FIG. 3. A type 649F photographic plate placed at the focal plane 27 was exposed to the light of a 15 milliwatt 6328A laser through the standard mask, and the exposed film was developed using Kodak type D165 low contrast developer to form the required filter. The resulting display of the nonperiodic errors (designated by the numerals 43—43) in the flawed mask of FIG. 10 is shown in FIG. 11.

While the invention has been described in connection with the inspection of an array-type photomask, it will be understood that any other suitable two-dimensional pattern containing a regular array of normally identical elements can be similarly inspected.

What is claimed is:

1. A method of isolating nonperiodic errors in a photomask containing a pattern formed by a regular array of normally identical elements mutually spaced apart by a predetermined distance, which comprises the steps of:

directing a spatially coherent beam of light at the pattern to diffract the light;

focusing the diffracted light on a filter containing a plurality of discrete opaque regions on a transparent field, the opaque regions being spaced by a distance inversely proportional to the predetermined distance to spatially modulate the intensity of the focused light; and reimaging the spatially modulated light to form an image exhibiting the nonperiodic errors in the pattern.

2. Apparatus for inspecting nonperiodic errors in a photomask containing a plurality of normally identical and regularly spaced elements arranged in a pattern forming a periodic array, which comprises:

means for directing a spatially coherent beam of light at the photomask so that the light is diffracted by the pattern thereon;

a first lens positioned to focus the light diffracted by the pattern;

a planar optical filter containing a distribution of discrete opaque regions on a transparent field, the opaque regions being spaced by a distance inversely proportional to the element spacing of the pattern, the filter being positioned at the focal plane of the first lens for spatially modulating the intensity of the light focused thereon by the first lens;

a second lens positioned to reimage the light transmitted by the filter to form a visual image representative of the non-periodic errors in the pattern;

image display means; and means for projecting the visual image onto the image display means.

3. Apparatus as defined in claim 2, in which the spatial distribution of opaque regions on the filter is defined by the spatial distribution of the interference function of the periodic array.

4. Apparatus as defined in claim 2, in which the spatial distribution of the opaque regions on the filter is defined by the spatial distribution of the diffraction pattern of a subtantially error-free photomask.

5. Apparatus for determining the presence of defects in a specimen pattern comprising:

a source of monochromatic collimated light for illuminating said pattern, optical means for generating from said pattern an image representing substantially the Fourier transform of said pattern, optical filter means receiving said image for blocking spatial frequency components of said image, said filter means comprising a pattern having relatively transparent and relatively opaque portions, the relatively opaque portion conforming to substantially the Fourier transform of an error-free reference pattern corresponding to said specimen pattern, and detector means for detecting the spatial frequency components of said immage not blocked by said filter means.

6. Apparatus as defined in claim 5 wherein said pattern is a microcircuit mask.

7. Apparatus as defined in claim 5 wherein said specimen, said filter means and said detector means lie substantially along the same optical axis.

* * * * *

UNITED STATES PATENT OFFICE
CERTIFICATE OF CORRECTION

Patent No. 4,000,949     Dated January 4, 1977

Inventor(s) L. S. Watkins

It is certified that error appears in the above-identified patent and that said Letters Patent are hereby corrected as shown below:

In the specification, Column 1, line 50, "spatical" should read --spatial--; line 58, "spactially" should read --spatially--. Column 3, line 18, "progressivve" should read --progressive--. Column 4, line 40, " 'standard" " should read --"standard"--.

In the claims, Column 8, claim 5, line 17, "immage" should read --image--.

Signed and Sealed this

Fifteenth Day of March 1977

[SEAL]

Attest:

RUTH C. MASON
Attesting Officer

C. MARSHALL DANN
Commissioner of Patents and Trademarks